United States Patent
Evsyukov et al.

(10) Patent No.: US 10,233,139 B2
(45) Date of Patent: Mar. 19, 2019

(54) ALKENYLPHENOXY-SUBSTITUTED 1,1-DIPHENYLETHYLENES, PROCESSES FOR THEIR PREPARATION, AND THEIR USE

(71) Applicant: Evonik Technochemie GmbH, Dossenheim (DE)

(72) Inventors: Sergey Evsyukov, Ludwigshafen (DE); Tim Pohlmann, Nidderau (DE); Horst Stenzenberger, Heidelberg (DE); Matthijs Ter Wiel, Dossenheim (DE)

(73) Assignee: Evonik Technochemie GmbH, Dossenheim (DE)

( * ) Notice: Subject to any disclaimer, the term of this patent is extended or adjusted under 35 U.S.C. 154(b) by 0 days.

(21) Appl. No.: 15/742,560

(22) PCT Filed: Sep. 2, 2016

(86) PCT No.: PCT/EP2016/070687
§ 371 (c)(1),
(2) Date: Jan. 8, 2018

(87) PCT Pub. No.: WO2017/045932
PCT Pub. Date: Mar. 23, 2017

(65) Prior Publication Data
US 2018/0201561 A1    Jul. 19, 2018

(30) Foreign Application Priority Data

Sep. 16, 2015  (EP) .................... 15185476

(51) Int. Cl.
| C07C 43/285 | (2006.01) |
| C08F 216/16 | (2006.01) |
| C08F 222/40 | (2006.01) |
| C08L 79/08  | (2006.01) |
| C08G 73/12  | (2006.01) |
| C08J 3/24   | (2006.01) |
| C09J 179/08 | (2006.01) |

(52) U.S. Cl.
CPC .......... *C07C 43/285* (2013.01); *C08F 216/16* (2013.01); *C08F 216/165* (2013.01); *C08F 222/40* (2013.01); *C08G 73/126* (2013.01); *C08J 3/242* (2013.01); *C08J 3/247* (2013.01); *C08L 79/085* (2013.01); *C09J 179/085* (2013.01); *C08F 2222/404* (2013.01); *C08F 2222/408* (2013.01)

(58) Field of Classification Search
CPC .... C07C 43/285; C08F 216/16; C08F 222/40; C08F 2222/404; C08F 216/165; C08F 2222/408; C09J 179/085; C08L 79/085; C08J 3/242; C08J 3/247; C08G 73/126
See application file for complete search history.

(56) References Cited

U.S. PATENT DOCUMENTS

| 3,663,625 A | | 5/1972 | Neville | |
| 4,100,140 A | | 7/1978 | Zahir et al. | |
| 5,025,095 A | * | 6/1991 | Blyakhman | C08F 222/40 528/154 |
| 5,037,689 A | * | 8/1991 | Boyd | C08J 5/24 428/113 |
| 5,134,214 A | * | 7/1992 | Bruza | C08F 222/40 526/262 |

FOREIGN PATENT DOCUMENTS

EP    046968 A1 *  2/1992  ............. C08G 73/12

OTHER PUBLICATIONS

U.S. Pat. No. 9,828,468, Nov. 28, 2017, 2016/0053054, Evsyukov et al.
U.S. Appl. No. 15/551,923, filed Feb. 1, 2018, 2018/0030208, Evsyukov et al.
International Search Report and Written Opinion dated Nov. 11, 2016, in PCT/EP2016/070687 filed Sep. 2, 2016.
European Search Report dated Mar. 21, 2016, in European Patent Application No. 15185476.7 filed Sep. 16, 2015.

* cited by examiner

*Primary Examiner* — Rosalynd A Keys
(74) *Attorney, Agent, or Firm* — Oblon, McClelland, Maier & Neustadt, L.L.P.

(57) ABSTRACT

The present invention relates to compounds according to formula (I) and to heat-curable compositions based on polymaleimide resin systems comprising such compounds as co-monomers: wherein $R^1$ is hydrogen or an alkenylphenoxy group, $R^2$ is an alkenylphenoxy group, and $R^3$ is hydrogen or an alkyl group with 1 to 4 carbon atoms. The present invention also relates to cross-linked resins obtainable by curing such compositions. Compounds of the present invention can be used amongst others in fields like structural adhesives, matrix resins for fiber prepregs, molding compounds, as well as structural and/or electrical composites.

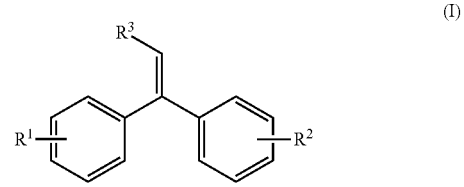

(I)

12 Claims, No Drawings

ALKENYLPHENOXY-SUBSTITUTED 1,1-DIPHENYLETHYLENES, PROCESSES FOR THEIR PREPARATION, AND THEIR USE

FIELD OF THE INVENTION

The present invention relates to alkenylphenoxy-substituted 1,1-diphenylethylenes and to heat-curable resin compositions based on polymaleimide resin systems comprising such alkenylphenoxy-substituted 1,1-diphenylethylenes as co-monomers. The present invention also relates to cross-linked resins obtainable by curing such compositions. Compounds of the present invention can be used amongst others in the following fields: Structural adhesives, matrix resins for fiber prepregs, moulding compounds, as well as structural and/or electrical composites.

BACKGROUND

Curable thermosetting compositions based on polymaleimide building blocks and co-monomers are established resins for fiber composites, adhesives, moulding and potting compounds. These resins are known for their high temperature resistance.

The co-monomer part of the composition influences several uncured and cured resin properties. Importantly, a suitable choice of this co-monomer part is required for modifying the processing properties of the uncured resin, in particular to adjust rheological properties such as flow and viscosity and to influence the cure kinetic properties.

Desired properties of the cured polymaleimide/co-monomer system include high glass transition temperature (Tg), high modulus retention at temperatures around 250° C., high heat resistance in terms of thermal oxidative stability (TOS) and durability, high toughness and damage tolerance and temperature cycling resistance to microcracking. Further desired properties include low moisture and solvent uptake and low dielectric constant (DC).

Many chemical concepts have been devised for generating polymaleimide/co-monomer systems. For applications as resins for fiber reinforced composites, structural adhesives and electrical and electronic appliances polymaleimide/alkenylphenol and polymaleimide/alkenylphenoxy based systems were found to be the most successful.

Alkenylphenol comonomers are disclosed in U.S. Pat. No. 4,100,140 (1978).

Curable thermosetting compositions based on polymaleimides and alkenylphenoxy compounds are known, for example, from U.S. Pat. No. 4,789,704 (1988), U.S. Pat. No. 4,826,929 (1989), U.S. Pat. No. 4,808,717 (1989), U.S. Pat. No. 4,962,161 (1990), U.S. Pat. No. 5,120,824 (1992), U.S. Pat. No. 4,873,284 (1989), U.S. Pat. No. 5,023,310 (1991), U.S. Pat. No. 5,023,310 (1991), U.S. Pat. No. 5,070,154 (1991) as well as US 2008/0075965A1 (2008), and CN104628544A (2015).

Desirable properties of uncured bismaleimide/co-monomer systems with respect to their use for composites and fiber reinforced composites in particular, include low viscosity at processing temperature, low processing temperature, sufficient pot life at processing temperature, good storage stability in the form of resins and intermediate products such as prepregs, glues or compounds as well as fast cure kinetics (fast reaction of co-monomers and polymaleimides) during manufacture of composites.

Few investigations relating to fast curing bismaleimide/co-monomer systems have been conducted so far, which is unfortunate in view of the fact that fast cure kinetics enable curing in short periods of time thus facilitating processing to be performed in an advantageous manner. U.S. Pat. No. 4,288,583 (Zahir, Wyler, 1981) discloses the results of one such investigation. In particular, U.S. Pat. No. 4,288,583 discloses mixtures of polymaleimides and propenyl-substituted phenols, e.g. o,o'-di(1-propenyl)bisphenols, as fast curing polymaleimide/co-monomer systems. CN104628544A (Liu et al., 2015) as well is directed at fast curing systems and discloses polymaleimide/trifunctional propenyl-endcapped co-monomer systems which provide fast curing kinetics due to their triplicate functionality.

Cured products obtained from the bismaleimide/co-monomer systems disclosed in U.S. Pat. No. 4,288,583, however, exhibit a pronounced tendency to absorb water (particularly pronounced under hot/wet conditions) resulting in several disadvantageous characteristics of the respective products, including the following: lowered glass transition temperature (Tg), weakened mechanical properties at elevated temperatures, increased tendency to suffer from microcracks under conditions of thermal cycling when used in fibre reinforced composites, impaired electrical properties (increased dielectric constant). The polymaleimide/trifunctional propenyl-endcapped co-monomer systems disclosed in CN104628544A, on the other hand, suffer from poor processability as viscosity is increased significantly by the trifunctional co-monomers.

In view of the above an object of the present invention resided in providing co-monomers for use in polymaleimide/co-monomer systems as well as such polymaleimide/co-monomer systems characterized by fast cure kinetics (fast reaction of co-monomers and polymaleimides) and good processing properties, yielding copolymers with a low tendency to absorb water thus resulting in copolymers with (i) good mechanical properties at elevated temperatures and/or (ii) a low tendency to suffer from microcracks under conditions of thermal cycling and/or (iii) good electrical properties (low dielectric constant).

DETAILED DESCRIPTION OF THE INVENTION

This object is achieved by alkenylphenoxy-substituted 1,1-diphenylethylenes of formula (I)

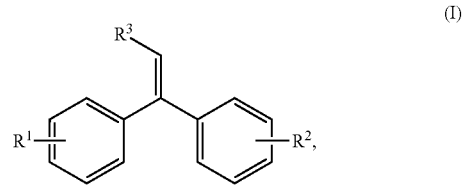

wherein $R^1$ is hydrogen or an alkenylphenoxy group,
$R^2$ is an alkenylphenoxy group, and
$R^3$ is hydrogen or an alkyl group with 1 to 4 carbon atoms.

Interestingly, while U.S. Pat. No. 4,789,704 discloses resins comprised of bismaleimides and alkenylphenoxy ethers which are based on polyaddition products of polyfunctional epoxy resins and o-allylphenol and/or eugenol, thus bearing some structural resemblance to the co-monomers disclosed under the present invention, these allylphenoxy-substituted epoxies yield mixtures with bismaleimides that are slow curing therefore requiring extended cure times.

In preferred embodiments alkenylphenoxy groups $R^1$ and $R^2$ are independently selected from the following structures:

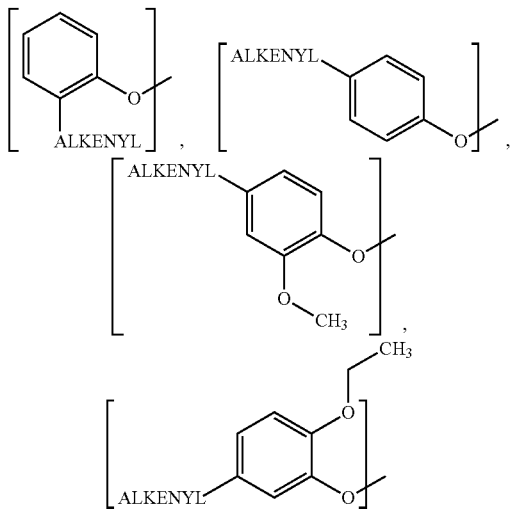

in which the ALKENYL residue is a 1-alkenyl group with 2 to 6 carbon atoms or a 2-alkenyl group with 3 to 6 carbon atoms.

In further preferred embodiments of the present invention $R^1$ and $R^2$ in formula (I) are

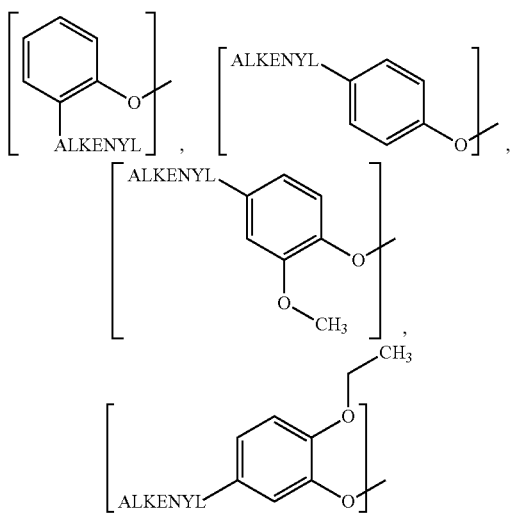

in which the ALKENYL residue is a 1-alkenyl group with 2 to 6 carbon atoms.

In further preferred embodiments of the present invention $R^1$ and $R^2$ in formula (I) are independently selected from the following structures:

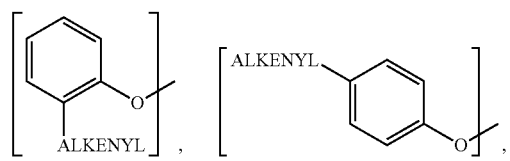

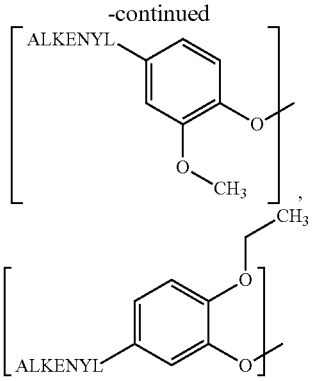

in which the ALKENYL residue is a 1-alkenyl group with 2 to 3 carbon atoms.

Curable Compositions of the Invention

In another aspect the present invention further relates to curable compositions comprising:

i) at least one alkenylphenoxy-substituted 1,1-diphenylethylene of formula (I)

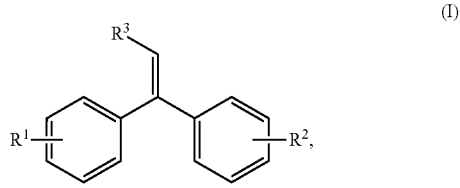

wherein $R^1$ is hydrogen or an alkenylphenoxy group,
$R^2$ is an alkenylphenoxy group, and
$R^3$ is hydrogen or an alkyl group with 1 to 4 carbon atoms;
ii) at least one polyimide of formula (II)

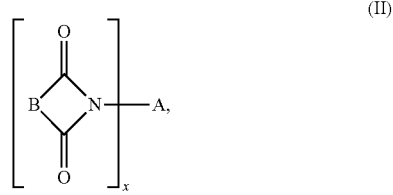

wherein
B is a difunctional group containing a carbon-carbon double bond, and
A is an x-functional group; and
x is an integer $\geq 2$.

In preferred curable compositions of the present invention alkenylphenoxy groups $R^1$ and $R^2$ in formula (I) are independently selected from the following structures

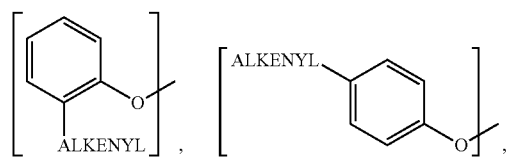

-continued

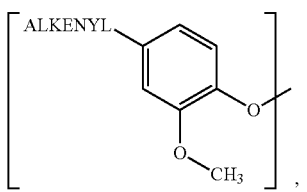

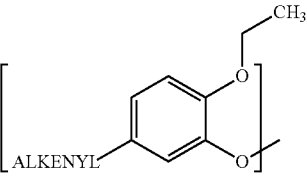

in which the ALKENYL residue is a 1-alkenyl group with 2 to 6 carbon atoms or a 2-alkenyl group with 3 to 6 carbon atoms.

In preferred curable compositions of the present invention the x-functional group A in the polyimide according to formula (II), is selected from the following difunctional groups:

a) alkylene group with 2 to 12 carbon atoms;
b) cycloalkylene group with 5 to 6 carbon atoms;
c) heterocyclic group with 4 to 5 carbon atoms and at least one nitrogen, oxygen, or sulphur atom in the ring;
d) mono- or dicarbocyclic group;
e) bridged multicyclic group consisting of at least two groups selected from the following: monocarbocyclic aromatic groups, dicarbocyclic aromatic groups, cycloalkylene groups; wherein these groups are linked to each other by direct carbon-carbon bonds or by divalent groups; wherein preferably the divalent groups are selected from the following: oxy-group, thio-group, alkylene-group with 1 to 3 carbon atoms, sulfone-group, methanone-group, or one of the following groups

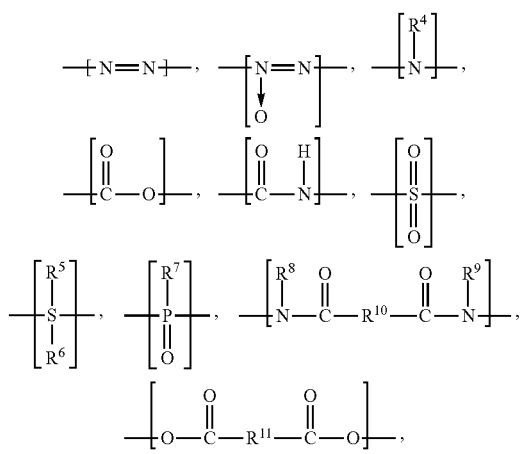

wherein $R^4$, $R^5$, $R^6$, $R^7$, $R^8$, $R^9$ are independently alkyl groups with 1 to 6 carbon atoms; and
$R^{10}$ and $R^{11}$ are independently alkylene groups with 1 to 6 carbon atoms;

f) group defined by formula (III)

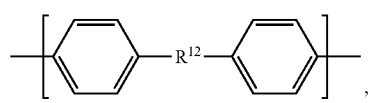

(III)

wherein $R^{12}$ is one of the following groups

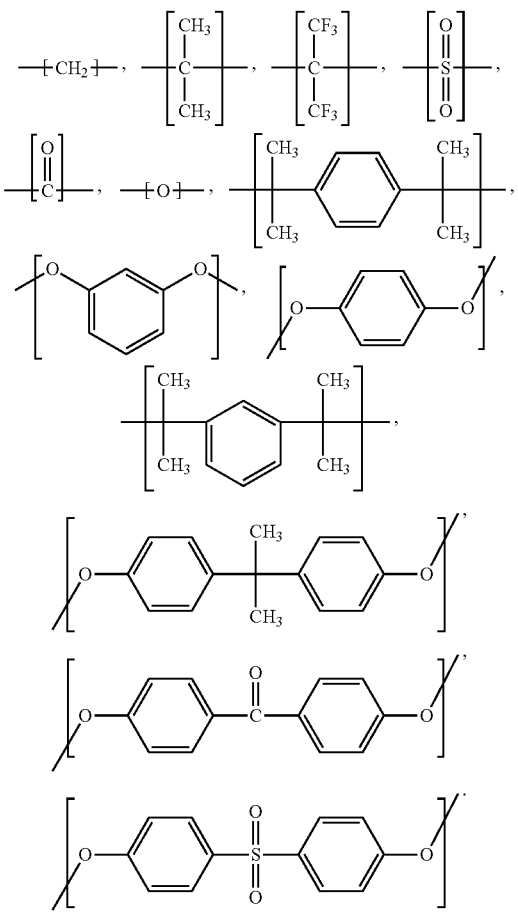

In preferred curable compositions of the present invention B in the polyimide according to formula (II), is selected from the following difunctional groups:

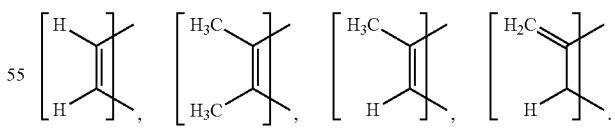

In further preferred curable compositions of the present invention the polyimide according to formula (II) is selected from the following:
4,4'-bismaleimidodiphenylmethane, bis(3-methyl-5-ethyl-4-maleimidophenyl)methane, bis(3,5-dimethyl-4-maleimidophenyl)methane, 4,4'-bismaleimidodiphenylether, 4,4'-bismaleimidodiphenylsulfone, 3,3'-bismaleimidodiphenylsulfone, bismaleimidodiphenylindane, 2,4-bismaleimidotoluene, 2,6-bismaleimidotoluene, 1,3-bismaleimidobenzene, 1,2-bismaleimidobenzene, 1,4-bismaleimidobenzene, 1,2-bismaleimidoethane, 1,6-bismaleimidohexane, 1,6-bismaleimido-(2,2,4-trimethyl)hexane, 1,6-bismaleimido-(2,4,4-trimethyl)hexane, 1,4-bis(maleimidomethyl)cyclohexane, 1,3-bis(maleimidomethyl)cyclohexane, 1,4-bismaleimidodicyclohexylmethane, 1,3-bis(maleimidomethyl)benzene, 1,4-bis(maleimidomethyl)benzene.

In further preferred curable compositions of the present invention $R^1$ and $R^2$ in formula (I) are independently selected from the following structures

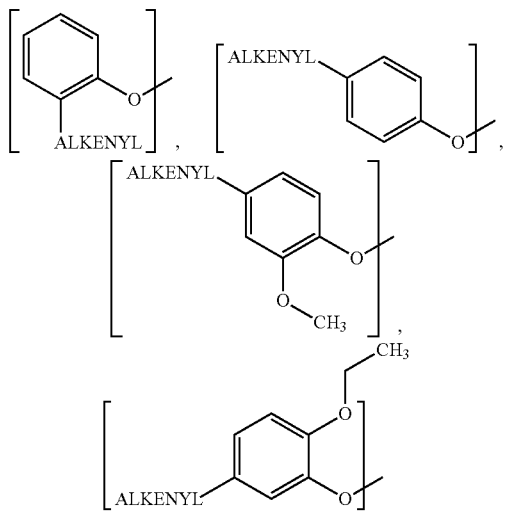

in which the ALKENYL residue is a 1-alkenyl group with 2 to 6 carbon atoms,
and the polyimide according to formula (II) is selected from the following:

4,4'-bismaleimidodiphenylmethane, bis(3-methyl-5-ethyl-4-maleimidophenyl)methane, bis(3,5-dimethyl-4-maleimidophenyl)methane, 4,4'-bismaleimidodiphenylether, 4,4'-bismaleimidodiphenylsulfone, 3,3'-bismaleimidodiphenylsulfone, bismaleimidodiphenylindane, 2,4-bismaleimidotoluene, 2,6-bismaleimidotoluene, 1,3-bismaleimidobenzene, 1,2-bismaleimidobenzene, 1,4-bismaleimidobenzene, 1,2-bismaleimidoethane, 1,6-bismaleimidohexane, 1,6-bismaleimido-(2,2,4-trimethyl)hexane, 1,6-bismaleimido-(2,4,4-trimethyl)hexane, 1,4-bis(maleimidomethyl)cyclohexane, 1,3-bis(maleimidomethyl)cyclohexane, 1,4-bismaleimidodicyclohexylmethane, 1,3-bis(maleimidomethyl)benzene, 1,4-bis(maleimidomethyl)benzene.

In another embodiment the present invention further relates to curable compositions as defined above further comprising one or more cure inhibitors to retard the polymerisation reaction, thus modifying processability and storage stability of the compositions and intermediate products, such as prepregs, moulding compounds and resin solutions. Suitable cure inhibitors are Hydroquinone, 1,4-Naphthoquinone, lonole and phenothiazine which are used at concentrations between 0.1 wt % and 2.0 wt %, based on the total weight of the composition. It is advantageous to dissolve the inhibitor in one of the components prior to the preparation of the mixture.

In another embodiment the present invention further relates to curable compositions as defined above further comprising one or more cure accelerators in order to accelerate the curing process. Typically cure accelerators are added in an amount of 0.01 wt % to 5 wt %, preferably in an amount of 0.1 wt % to 2 wt % based on the total weight of the curable composition. Suitable cure accelerators include ionic and free radical polymerization catalysts. Examples for free radical polymerization catalysts include (a) organic peroxides such as ditertiary butyl peroxide, diamylperoxide and t-butylperbenzoate and (b) azo compounds such as azobisisobutyronitrile. Examples of ionic catalysts are alkali metal compounds, tertiary amines such as triethylamine, dimethylbenzylamine, dimethylaniline, azabicyclooctane, heterocyclic amines such as quinoline, N-methylmorpholine, methylimidazole and phenylimidazole and phosphorous compounds such as triphenylphosphine and quaternary phosphonium halides. The cure accelerators can be admixed with the components of the curable composition or may be added during the production of the prepolymers either by a powder blending process or by a solvent blending process.

Curable Compositions Comprising a Secondary Co-Monomer Component

In another aspect the present invention further relates to curable compositions comprising in addition to the at least one Alkenylphenoxy-1,1-diphenylethylene according to formula (I) as defined above and the at least one polyimide of formula (II) as defined above, a secondary co-monomer component, which consists of one or a combination of at least two co-monomers selected from the following: alkenylphenol, alkenylphenyl ether, alkenyl phenol ether, polyamine, aminophenol, aminoacid hydrazide, cyanate ester, diallyl phthalate, triallyl isocyanurate, triallyl cyanurate, styrene, divinylbenzene, wherein the secondary co-monomer component represents between 1 wt % and 30 wt % of the total composition.

These secondary co-monomers may act as diluents for the compositions of the invention modifying their viscosity and/or processability. The secondary co-monomers may also act as cure accelerators or as cure retardants in the compositions of the invention.

Preferably the secondary co-monomer component consists of one or a combination of at least two co-monomers selected from the following:
(a) a compound of formula (IV)

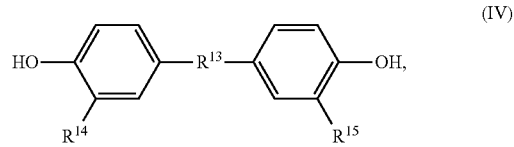

wherein
$R^{13}$ is a difunctional group, and
$R^{14}$ and $R^{15}$ are independently alkenyl groups with 2 to 6 carbon atoms;
(b) a compound of formula (V)

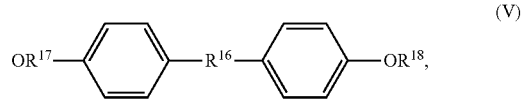

wherein
R¹⁶ is a difunctional group, and
R¹⁷ and R¹⁸ are independently alkenyl groups with 2 to 6 carbon atoms;
(c) a compound of formula (VI)

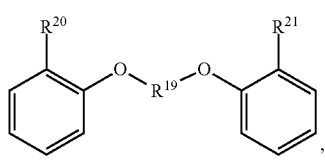
(VI)

wherein
R¹⁹ is a difunctional group, and
R²⁰ and R²¹ are independently alkenyl groups with 2 to 6 carbon atoms;
(d) a compound of formula (VII)

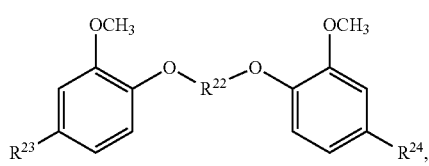
(VII)

wherein
R²² is a difunctional group, and
R²³ and R²⁴ are independently alkenyl groups with 2 to 6 carbon atoms;
(e) a compound of formula (VIII)

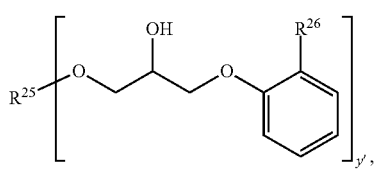
(VIII)

wherein
R²⁵ is a y'-functional group, and
R²⁶ is an alkenyl group with 2 to 6 carbon atoms, and
y' is an integer ≥2;
(f) a compound of formula (IX)

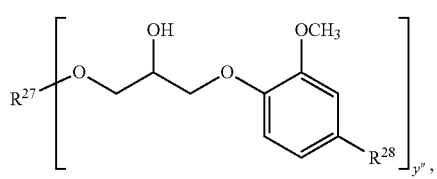
(IX)

wherein
R²⁷ is a y''-functional group, and
R²⁸ is an alkenyl group with 2 to 6 carbon atoms, and
y'' is an integer ≥2.
Preferably residues R¹³ in formula IV and R¹⁶ in formula V are selected from the following groups:

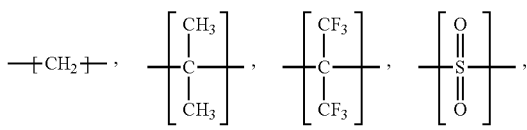
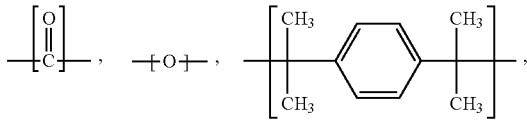
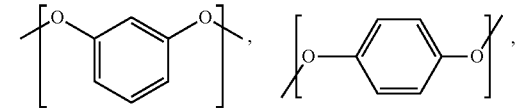
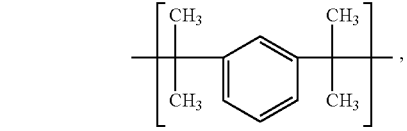
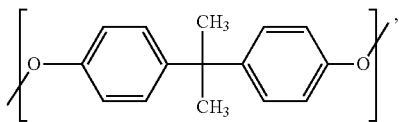
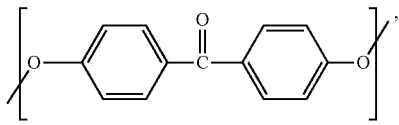
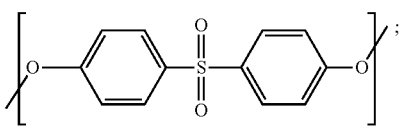

and residues R¹⁹ in formula VI and R²² in formula VII are selected from the following groups

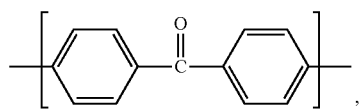
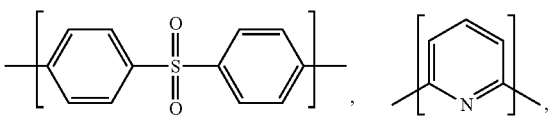
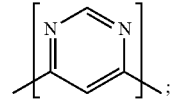

and residues R²⁵ in formula VIII and R²⁷ in formula IX are difunctional groups selected from the following groups

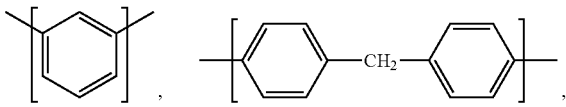

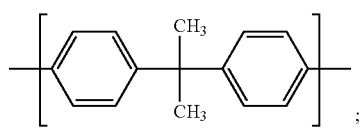

and residues $R^{26}$ in formula VIII and $R^{28}$ in formula IX are 1-propen-1-yl or 2-propen-1-yl groups.

Preferably, the secondary co-monomer component consists of one or a combination of at least two co-monomers selected from the following:

2,2'-diallylbisphenol-A, bisphenol-A diallyl ether, bis(o-propenylphenoxy)benzophenone, m-aminobenzhydrazide, bisphenol-A dicyanate ester, diallyl phthalate, triallyl isocyanurate, triallyl cyanurate, styrene, divinylbenzene.

Synthesis of Compounds According to Formula (I)

The alkenylphenoxy-substituted 1,1-diphenylethylenes of the present invention can be prepared by a variety of well known methods from appropriate starting materials such as alkenylphenoxy-substituted benzophenones or alkenylphenoxy-alkyl methanones. Three methods for the synthesis of alkenylphenoxy-substituted 1,1-diphenylethylenes are outlined below. Two synthesis routes are based on Grignard Reactions utilizing the appropriate alkenylphenoxy-substituted benzophenone (route 1) or alkenylphenoxy, alkyl methanone (route 2) and the appropriate alkyl- (route 1) or arylmagnesium halide (route 2). The third synthesis route is based on a Wittig Reaction of alkenylphenoxy-substituted benzophenone with the appropriate triphenylalkylphosphorane (route 3).

Route 1

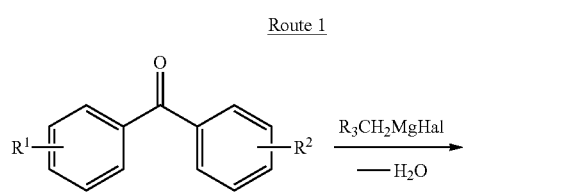

Route 2

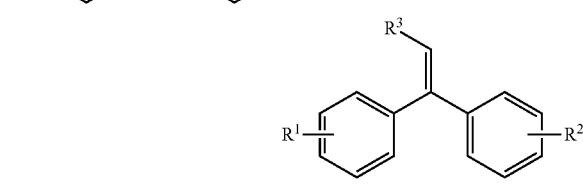

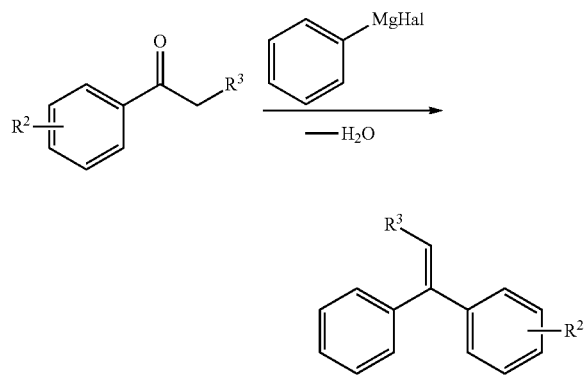

Route 3

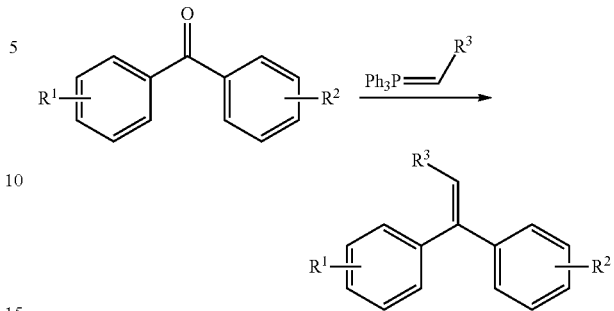

In these structures $R^1$ signifies hydrogen or an alkenylphenoxy group selected from the following structures

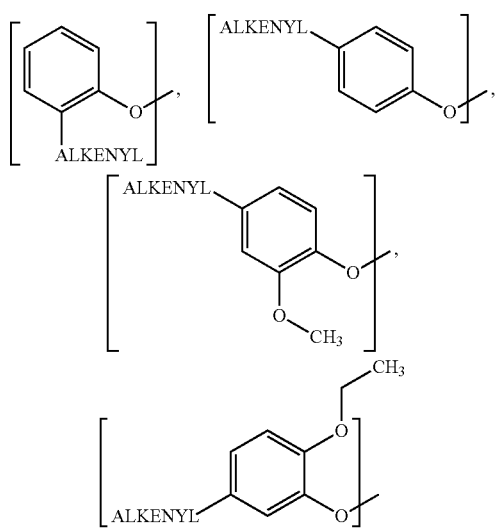

in which the ALKENYL residue is a 1-alkenyl group with 2 to 6 carbon atoms or a 2-alkenyl group with 3 to 6 carbon atoms.

The starting materials for the new alkenylphenoxy-substituted 1,1-diphenylethylenes, the alkenylphenoxy-substituted benzophenones are known from U.S. Pat. No. 4,789,704 and the alkenylphenoxy, alkyl methanones can be obtained by reaction of 4-fluoro alkyl methanones with alkenylphenols in the presence of potassium carbonate via a nucleophilic displacement reaction.

Processes for the Manufacture of Curable Compositions of the Invention

In one aspect, the present invention further relates to processes for the manufacture of curable compositions according to the invention, comprising the step of blending the components of the composition using a powder-, melt-, solvent-assisted or other blending process resulting in solid, low-melting, or tacky curable compositions.

Melt Blending Process

In one aspect, the present invention relates to processes for the manufacture of curable compositions of the invention, comprising the step of:

blending the components of a composition comprising a co-monomer component of the invention and a polyimide component as defined above at a temperature ranging from 70° C. to 250° C. to obtain curable compositions as low melting low viscosity masses (resins).

In the practice of this method, the blending temperatures may be varied over a relatively wide range. In one embodiment, the method is carried out at temperatures from 90° C. to 170° C., preferably from 100° C. to 160° C.

Solution Blending Process

In one aspect, the present invention relates to processes for the manufacture of curable compositions of the invention, comprising the step of:

dissolving the components of a composition comprising a co-monomer component of the invention and a polyimide component as defined above, in a solvent or diluent, and stripping off the solvent or diluent, to obtain a curable composition as a solvent-free, low melting, low viscosity mass (resin).

In one embodiment, the co-monomer component of the invention and the polyimide component as defined above are dissolved in the solvent at elevated temperature.

Suitable solvents and diluents are all customary inert organic solvents. They include but are not limited to ketones such as acetone, methylethylketone, cyclohexanone; glycol ethers such as methyl glycol, methyl glycol acetate, propylene glycol monomethyl ether (methyl proxitol), methyl proxitol acetate, diethylene glycol, and diethylene glycol monomethyl ether; toluene and xylene, preferably in combination with 1,3-dioxolane as a co-solvent.

In a preferred embodiment, the solvent is 1,3-dioxolane or a 1,3-dioxolane-containing solvent.

In one embodiment, the amount of 1,3-dioxolane in the solvent mixture ranges from 20 wt % to 80 wt %, e.g. from 30 wt % to 70 wt % or from 40 wt % to 60 wt %.

In the practice of the processes for the manufacture of the curable composition, i.e. in the melt process and in the solution process, the molar ratio between the unsaturated imide groups and reactive alkenyl groups in the composition ranges from 1.0 to 0.1, e.g. from 1.0 to 0.2, from 1.0 to 0.3, from 1.0 to 0.4, from 1.0 to 0.5, from 1.0 to 0.6, from 1.0 to 0.7 or from 1.0 to 0.8 in order to achieve the desired cure kinetics.

Other Blending Processes

Preparation of the curable compositions of this invention can be carried out without any diluent or solvent in that the components as powders, pastes or liquids are intimately mixed, if necessary at elevated temperature, to obtain a homogeneous blend of the monomers or a prepolymer depending on the duration of the temperature treatment. This process cannot be scaled up to reasonable volumes due to the high reactivity of the mixture. An extruder process may be used to control and set the required melting temperature, to provide the necessary temperature for prepolymerization in the reaction zone and to set the time at temperature by the throughput. The extrudate, after cooling, may be a hot melt product or a solidified melt which can be milled to a resin powder.

Storage Stable Mixtures

For many technical applications of the curable compositions it is advantageous to retard polymerisation by the addition of reaction inhibitors in order to improve processability and storage stability before use. Suitable reaction inhibitors are hydroquinone, 1,4-naphthoquinone and phenothiazine which are used at concentrations between 0.1 wt % and 2.0 wt %, based on the total weight of the composition. It is advantageous to dissolve the inhibitor in one of the components prior to the preparation of the composition.

Compositions Comprising a Secondary Co-Monomer Component

In many cases the curable compositions of the present invention may be processed from the melt. In order to reduce melt viscosity and improve pot life of the resin a secondary co-monomer component may be added, which consists of one or more co-monomers selected from the following: alkenylphenol, alkenylphenyl ether, alkenyl phenol ether, polyamine, aminophenol, aminoacid hydrazide, cyanate ester, diallyl phthalate, triallyl isocyanurate, triallyl cyanurate, styrene, divinylbenzene, wherein the secondary co-monomer component represents between 1 wt % and 30 wt % of the total composition. Of these, allyl-type secondary co-monomer components such as diallylbisphenol-A, bisphenol-A diallylether, diallylphthalate, triallylisocyanurate and triallylcyanurate when added to the curable composition slow down polymerisation kinetics and therefore widen the processing window. Secondary co-monomer components like styrene or divinylbenzene are very effective in concentrations between 10 wt % and 20 wt % but accelerate polymersation kinetics, providing faster curing resins and lowering their polymerisation temperature. Therefore, secondary co-monomer components are an additional tool to modify cure velocity of the curable compositions of the invention. In cases where such secondary co-monomer components are used it is advantageous to first blend the alkenylphenoxy-substituted 1,1-diphenylethylene compound (I) with the secondary co-monomer component in the required proportion and then, in a second step, dissolve the polyimide part of the mixture in this blend, if necessary at elevated temperature.

Compositions Comprising Thermoplastic Toughening Modifier

Curable compositions of the present invention may further include from 0 wt % to about 30 wt %, based on the total weight of the composition, of a thermoplastic polymer such as, for example, a polyaryl ether, a polyaryl sulfone, a polyarylate, a polyamide, a polyaryl ketone, a polyimide, a polyimide-ether, a polyolefin, an ABS resin, a polydiene or diene copolymer or mixtures thereof. Thermoplastics such as polysulfons and phenoxy resins are particularly miscible with the curable compositions of the present invention, and may be used to adjust resin viscosity and control flow during cure. Thermoplastic polymers may also be added to improve the fracture toughness. Thermoplastic polymers can be added to the curable compositions as fine powders, or may be dissolved in either the alkenylphenoxy-substituted 1,1-diphenylethylene compound (I) or a secondary co-monomer component.

The curable compositions of the invention can be isolated by customary techniques and processes (cf. e.g. examples section).

Pre-Polymers of Curable Compositions of the Invention and Processes for their Manufacture In one aspect the present invention relates to the use of a curable composition as defined above for the preparation of a prepolymer.

It has been found that the curable compositions of the invention are useful for the preparation of partially cross-linked products (i.e. prepolymers). Prepolymers are prepared by heating curable compositions as defined above to temperatures of 80° C. to 350° C., preferably to 100° C. to 250° C. for a time sufficient to obtain a prepolymer which is still formable upon applying heat and/or pressure. Optionally this is performed in the presence of a cure catalyst or cure stabilizer.

Cure Accelerators

For some applications of the curable compositions of the present invention it is advantageous to accelerate the curing process by adding catalysts, typically in an amount of 0.01 wt % to 5 wt %, preferably in an amount of 0.1 wt % to 2 wt % based on the total weight of the curable composition. Suitable catalysts include ionic and free radical polymerization catalysts. Examples for free radical polymerization catalysts include (a) organic peroxides such as ditertiary butyl peroxide, diamylperoxide and t-butylperbenzoate and (b) azo compounds such as azobisisobutyronitrile. Examples of ionic catalysts are alkali metal compounds, tertiary amines such as triethylamine, dimethylbenzylamine, dimethylaniline, azabicyclooctane, heterocyclic amines such as quinoline, N-methylmorpholine, methylimidazole and phenylimidazole and phosphorous compounds such as triphenylphosphine and quaternary phosphonium halides. The catalysts can be admixed with the components of the curable composition or may be added during the production of the prepolymers either by a powder blending process or by a solvent blending process as described above.

In another aspect the present invention further comprises curable pre-polymers obtainable from curable compositions according to the invention, by a process comprising the step of heating the curable composition to a temperature in the range of 50° C. to 250° C., preferably to 70° C. to 170° C., for a time sufficient to obtain a pre-polymer, which is still formable upon the application of heat and/or pressure.

If the method is carried out in the presence of a solvent, high boiling point polar solvents such as dimethylformamide, dimethylacetamide, N-methylpyrrolidone, and butyrolactone can in principle be used. However, the use of such solvents generally yields prepolymers with high contents of residual solvents.

If the method is carried out in the presence of a solvent, in one embodiment low boiling solvent mixtures containing 1,3-dioxolane may be used. These preferably include, but are not limited to, solvent mixtures of 1,3-dioxolane with ketones such as acetone, methylethylketone, cyclohexanone or glycol ethers such as ethylene glycol ether, propylene glycol ether, butylene glycol ether and their acetates.

Due to the low boiling point of solvent mixtures comprising 1,3-dioxolane and the above-identified solvents, such solvent mixtures are useful for the preparation of solvent free prepolymers. Further, the so obtained prepolymers can be processed to void-free fiber-reinforced composites.

In one embodiment, the solvent mixture comprises up to 50 wt %, preferably up to 40 wt % of ketones such as acetone, methylethylketone, cyclohexanone, or glycol ethers such as ethylene glycol ether, propylene glycol ether, butylene glycol ether, and their acetates based on the total weight of the solvent mixture.

In one embodiment, a solution of the curable composition of the invention comprises from 30 wt % to 70 wt %, preferably from 40 wt % to 60 wt % of solvent, e.g. of 1,3-dioxolane, or solvent mixtures comprising 1,3-dioxolane, and the above-identified solvents. Such concentrations are typically used in industrial dip coating processes.

The prepolymers of the curable composition of the invention can be isolated by generally customary processes, e.g. by evaporation of the solvent if the subsequent use is solvent free.

The prepolymers which are obtained according to the method of the invention are still soluble in selected organic solvents. Further, the prepolymers of the invention are still fusible and formable upon the application of heat and/or pressure.

In another aspect, the present invention relates to a curable prepolymer obtainable according to a method as described above.

Crosslinked Polymers of the Curable Compositions of the Invention and Processes for their Manufacture In one aspect, the invention relates to the use of a curable composition as defined above or of a prepolymer as defined above for the preparation of a crosslinked polymer.

It has been found that the curable compositions and curable prepolymers of the invention are useful for the preparation of crosslinked polymers.

In one aspect, the invention relates to a method for the preparation of a crosslinked polymer comprising the step of: heating a curable composition as defined above or a curable prepolymer as defined above to a temperature ranging from 70° C. to 280° C. for a time sufficient to complete cure.

In the practice of this method, the reaction temperatures may be varied over a relatively wide range. In one embodiment, the method is carried out at temperatures from 80° C. to 270° C., more preferably from 90° C. to 260° C., most preferably from 100° C. to 250° C.

In another aspect the present invention further comprises crosslinked polymers obtainable from the curable compositions according to the invention by a process comprising the step of heating the curable composition to a temperature in the range of 70° C. to 280° C. for a time sufficient to obtain a polymer.

The conversion may take place with simultaneous shaping under pressure to obtain mouldings, laminates, adhesive bonds, and foams.

For these applications, it is possible to admix the curable composition with additives such as fillers, pigments, colorants, and flame retardants. Suitable fillers are glass- or carbon fibers, graphite, quartz, metal powders, and metal oxides. Mould release agents such as silicone oil, waxes, Zn and K-stearates may also be added.

In another aspect, the present invention relates to mouldings, laminates, adhesive bonds, and foams obtainable by processing of the curable composition and curable prepolymers of the invention.

Composite Materials of the Invention and Processes for their Manufacture

It has been found that curable compositions and prepolymers of the invention are useful for the preparation of composite materials.

Mixtures Containing Particulate Fillers

The curable compositions of the present invention can be processed by known methods of the powder moulding industry for producing mouldings, with curing taking place with simultaneous shaping under pressure. For these applications the curable compositions are admixed with additives such as fillers, colorants and flame retardants. Ideal fillers for example are short glass fibers, short carbon fibers or aramid fibers, particulate fillers such as quartz, silica, ceramics, metal powders and carbon powder. Depending on the technical application of the moulded article two or more different fillers may be used at the same time.

Applications

One of the preferred uses of the curable compositions of the present invention is as binders for fiber composites. For this application fibers such as glass, carbon or aramid in the form of rovings, fabrics, short fiber mats, or felts are impregnated with the curable composition, employing a solution of the said curable composition to impregnate said reinforcements. After drying off the solvent a prepreg is left, which in the second phase may be cured at a temperature between 180° C. and 350° C., optionally under pressure.

Melt Prepregs

A preferred application oft the curable compositions of the present invention is as hot-melt resins for fiber-reinforced composites. In order to obtain such fiber-reinforced composites the curable compositions are processed as hot melts to a resin film on a carrier foil, subsequently fibers, in the form of rovings or fabrics, are pressed into the molten resin film to form a prepreg. For this process curable compositions, which have a low viscosity at low temperature are advantageous in order to provide adequate impregnation of fiber rovings or fabric.

Laminates

One of the preferred applications of the curable compositions of the present invention is as resins for fiber laminates. Prepregs manufactured by either the solvent/solution- or the hot-melt process from glass-, carbon- or aramid fibers, in the form of fabriques or rovings, are stacked to provide a prepreg laminate, which subsequently is cured under pressure or in a vacuum bag at a temperature between 150° C. and 280° C. preferably between 170° C. and 260° C.

In one aspect, thus, the invention relates to a method for the preparation of a composite material comprising the steps of:
applying or blending a curable composition in form of a low-viscosity-melt stable resin obtainable according to the method as defined above, or a prepolymer as defined above, onto or with a fibrous or particulate reinforcement (filler); and subsequent curing.

In one embodiment, the curable composition or the prepolymer as defined above is applied onto or blended with a fibrous or particulate reinforcement (filler) with the use of standard processing techniques, e.g. with the use of the hot melt or solution-based prepregging, resin transfer moulding (RTM), resin infusion moulding (RIM), filament winding (FW) or compounding techniques.

Curing may be carried out at temperatures ranging from 70° C. to 280° C., preferably at temperatures ranging from 80° C. to 270° C., more preferably at temperatures ranging from 90° C. to 260° C., most preferably at temperatures ranging from 100° C. to 250° C. for a time sufficient to complete cure.

In another aspect the present invention further comprises processes for the manufacture of composite materials comprising the steps of combining a curable composition according to the invention or a curable pre-polymer according to the invention, with a fibrous or particulate reinforcement, and curing the resultant product.

In one embodiment, the composite material is a fiber-reinforced composite.

In one embodiment, the composite material is a particulate-filled composite.

In one aspect, the present invention relates to a method for the preparation of a composite material comprising the steps of:
(a) preparing a curable composition or a prepolymer thereof as defined above,
(b) applying a curable composition or a prepolymer thereof as defined above onto a fibrous reinforcement or blending with a particulate filler,
(c) curing the curable composition or prepolymer thereof as defined above at a temperature ranging from 70° C. to 280° C. for a time sufficient to complete cure, and
(d) simultaneously applying pressure to obtain the composite material.

Process step c) may be carried out at temperatures ranging from 70° C. to 280° C., preferably at temperatures ranging from 80° C. to 270° C., more preferably at temperatures ranging from 90° C. to 260° C., most preferably at temperatures ranging from 100° C. to 250° C. for a time sufficient to complete cure.

In the practice of process step c) the conversion of the curable compositions or prepolymers of the invention into the crosslinked (cured) polymer may be carried out, in the presence of a curing catalyst as defined above.

In the practice of process step d) shaping under pressure is performed to obtain the composites of the invention. Process steps c) and d) are carried out simultaneously.

A preferred application of the curable compositions of the invention is resins for fiber-reinforced composites. In order to obtain such fiber composites the curable compositions of the invention are processed as hot melts to resin film on a carrier foil, which is subsequently used to prepare prepolymers by pressing fibers in the form of rovings or fabrics into the resin film. For this process curable compositions, which have a low viscosity at low temperature are advantageous in order to provide adequate impregnation of fiber rowings or fabric.

In one aspect the present invention comprises composite materials obtainable by a process according to the invention.

Definitions

As used herein, including the accompanying claims, the terms, which are collectively used, have the following meanings.

As used herein, the term "curable" means that an original compound(s) or mixture material(s) can be transformed into a solid, substantially non-flowing material by means of chemical reaction, crosslinking, radiation crosslinking or the like.

As used herein, the term "mixture" means a physical or mechanical aggregation or a combination of two or more individual, chemically distinct compounds that are not chemically united.

As used herein, the term "polyimide component" means one polyimide or a mixture of two or more polyimides, preferably one polyimide or a mixture of two to four polyimides.

As used herein, the term "co-monomer" means a compound that can undergo polymerization or copolymerization, thereby contributing constitutional units to the essential structure of a polymer.

As used herein, the term "co-monomer component" means one co-monomer or a mixture of two or more co-monomers, preferably one co-monomer or a mixture of two to four co-monomers.

As used herein, the term "alkenylphenol" means organic compounds comprising at least one alkenyl-substituted phenol group. The term "alkenylphenol" comprises alkenylphenols, wherein two phenol groups are bridged via a difunctional group, e.g. alkenylbisphenols. Examples include 2,2'-diallyl-bisphenol A.

As used herein, the term "alkenylphenyl ether" means organic compounds comprising at least one alkenyloxyphenyl group, i.e. an ether group wherein the ether oxygen atom is connected on one hand to an alkenyl residue and on the other hand to a phenyl residue. The term "alkenylphenyl ether" comprises alkenylphenyl ethers, wherein two phenyl groups are bridged by a difunctional group, e.g. alkenylbisphenol ether. Examples include diallyl ether of bisphenol A.

As used herein, the term "alkenylphenol ether" means organic compounds comprising at least one alkenylphenoxy group, e.g. an ether group wherein the ether oxygen atom is connected on one hand to an alkenylphenyl group and on the other hand to a an alkyl or an aryl group. The term "alkenylphenol ether" comprises organic compounds, wherein two alkenylphenoxy groups are bridged by a difunctional group, e.g. by an aromatic group such as a benzophenone group. Examples include bis-(o-propenyl-phenoxy)benzophenone.

As used herein, the term "polyamine" means an organic compound having two or more primary amino groups —NH$_2$. Examples include, but are not limited to 4,4'-diaminodiphenylmethane, 4,4'-diaminodiphenylsulfone, 3,3'-diaminodiphenylsulfone, diaminodiphenylindane, m-phenylenediamine, p-phenylenediamine, 2,4-diaminotoluene, 2,6-diaminotoluene, m-xylylenediamine and aliphatic diamines such as ethylenediamine, hexamethylenediamine, trimethylhexamethylenediamine, 1,12-diaminododecane.

As used herein, the term "aminophenol" means amino-substituted phenols. Examples include m-aminophenol and p-aminophenol.

As used herein, the term "amino acid hydrazides" means any hydrazides of amino acids. Examples include m-aminobenzhydrazide and p-aminobenzhydrazide.

As used herein, the term "cyanate ester" means a bisphenol or polyphenol, e.g. novolac, derivative, in which the hydrogen atom of the phenolic OH group is substituted by a cyano-group, resulting in an —OCN group. Examples include bisphenol A dicyanate ester, commercially available as, e.g. Primaset BADCy from Lonza or AroCy B-10 from Huntsman, as well as other Primaset or AroCy types, e.g. bis(3,5-dimethyl-4-cyanatophenyl)methane (AroCy M-10), 1,1-bis(4-cyanatophenyl)ethane (AroCy L-10), 2,2-bis(4-cyanatophenyl)-1,1,1,3,3,3-hexafluoropropane (AroCy F-10), 1,3-bis(1-(4-cyanatophenyl)-1-methylethylidene) benzene (AroCy XU-366), di(4-cyanatophenyl)thioether (AroCy RDX-80371; AroCy T-10), bis(4-cyanatophenyl) dichloromethylidenemethane (AroCy RD98-228), bis(4-cyanatophenyl)octahydro-4,7-methanoindene (AroCy XU-71787.02L), as well as bis(4-cyanatophenyl)methane, bis(3-methyl-4-cyanatophenyl)methane, bis(3-ethyl-4-cyanatophenyl)methane, di(4-cyanatophenyl)ether, 4,4-dicyanatobiphenyl, 1,4-bis(1-(4-cyanatophenyl)-1-methylethylidene)benzene, resorcinol dicyanate. A preferred example is bisphenol A dicyanate ester.

Any bond intersected by a bracket indicates a bond that connects the moiety within the bracket to other moieties of the same compound. For example, in the group shown below the two bonds of the ethenyl group intersected by the bracket on the right side connect this moiety to other moieties of the compound containing this ethenyl group.

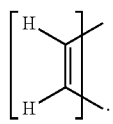

As used herein, the term "halogen" means a fluorine, chlorine, bromine or iodine atom, preferably a fluorine or chlorine atom, more preferably a fluorine atom.

As used herein, "alkyl" means a straight-chain or branched alkyl group. The term "alkyl with n to m carbon atoms" means an alkyl group with n to m carbon atoms. If not denoted otherwise, "alkyl" means an alkyl with 1 to 6 carbon atoms. In the context of the present invention, preferred alkyl groups are straight-chain or branched alkyl groups with 1 to 4 carbon atoms. Examples of straight-chain and branched alkyl groups include, but are not limited to methyl, ethyl, propyl, isopropyl, butyl, isobutyl, tert.-butyl, the isomeric pentyls, the isomeric hexyls, preferably methyl and ethyl and most preferred methyl.

As used herein, "alkylene" means a difunctional alkyl group. The term "alkylene with n to m carbon atoms" means an alkylene group with n to m carbon atoms. If not denoted otherwise, "alkylene" means an alkylene with 1 to 12 carbon atoms. In the context of the present invention, preferred alkylene groups are alkylene groups with 1 to 9 carbon atoms, more preferably from 1 to 6 carbon atoms. Examples include, but are not limited to methylene, ethylene, propylene, butylene, hexamethylene and 2,2,4-trimethylhexamethylene. Particularly preferred is 2,2,4-trimethylhexamethylene.

As used herein, "alkenylene" means a difunctional alkenyl group. The term "alkenylene with n to m carbon atoms" means an alkenylene group with n to m carbon atoms. If not denoted otherwise, "alkenylene" means an alkenylene with 2 to 12 carbon atoms. In the context of the present invention, preferred alkenylene groups are alkenylene groups with 2 to 10 carbon atoms, more preferably from 2 to 6 carbon atoms. Examples include, but are not limited to ethenylene, propenylene, and butenylene. Particularly preferred is ethenylene.

As used herein, "alkoxy" means a straight-chain or branched alkyl group, which is bonded to the compound via an oxygen atom (—O—). The term "alkoxy with n to m carbon atoms" means an alkoxy with n to m carbon atoms. If not denoted otherwise, "alkoxy" means a straight-chain or branched alkyl group with 1 to 6 carbon atoms. In the context of the present invention, preferred alkoxy groups are straight-chain or branched alkoxy groups with 1 to 4 carbon atoms.

As used herein, "alkenyl" means a straight-chain or branched hydrocarbon group comprising a carbon-carbon double bond. The term "alkenyl with n to m carbon atoms" means an alkenyl with n to m carbon atoms. If not denoted otherwise, "alkenyl" means a straight-chain or branched hydrocarbon group comprising a carbon-carbon double bond in any desired position and 2 to 10 carbon atoms. In the context of the present invention, preferred alkenyl groups comprise a carbon-carbon double bond in any desired position and 2 to 6, more preferably 2 to 4 carbon atoms. Examples of alkenyl groups include, but are not limited to ethenyl, 1-propenyl, 2-propenyl, isopropenyl, 1-butenyl, 2-butenyl, 3-butenyl and isobutenyl. Preferred examples are 1-propenyl and 2-propenyl.

As used herein the term "monocarbocyclic group" means a "monocarbocyclic aliphatic group" or a "monocarbocyclic aromatic group".

As used herein the term "dicarbocyclic group" means a "dicarbocyclic aliphatic group" or a "dicarbocyclic aromatic group" group.

As used herein the term "monocarbocyclic aliphatic group" means a cycloalkylene group.

As used herein, "cycloalkyl" means a monofunctional carbocyclic saturated ring system. The term "cycloalkyl with n to m carbon atoms" means a cycloalkyl with n to m carbon atoms. If not denoted otherwise, "cycloalkyl" means a cycloalkyl group with 5 to 6 carbon atoms. Examples of cycloalkyl groups include, but are not limited to cyclopropanyl, cyclobutanyl, cyclopentanyl, cyclohexanyl, cycloheptanyl or cyclooctanyl, preferably cyclopentanyl and cyclohexanyl.

As used herein, "cycloalkylene" means a difunctional carbocyclic saturated ring system. The term "cycloalkylene with n to m carbon atoms" means a cycloalkylene with n to m carbon atoms. If not denoted otherwise, "cycloalkylene" means a cycloalkylene group with 3 to 8 carbon atoms. In the context of the present invention preferred cycloalkylene groups are cycloalkylene groups with 5 to 7, more preferably 5 or 6 carbon atoms. Examples include, but are not limited to cyclopropylene, cyclobutylene, cyclopentylene, cyclohexylene, cycloheptylene or cyclooctylene, preferably cyclopentylene and cyclohexylene.

As used herein, "dicarbocyclic aliphatic group" means a difunctional bicyclic condensed, bridged or fused saturated ring system. If not denoted otherwise, "dicarbocyclic aliphatic group" means a difunctional bicyclic condensed, bridged or fused saturated ring system with 9 to 20 carbon atoms. Examples include, but are not limited to decalinyl, hydrindanyl and norbornyl.

As used herein, the term "mono- or dicarbocyclic aromatic group" means a difunctional mono- or dicyclic aromatic system, preferably with 6 to 12 carbon atoms, preferably a monocyclic aromatic system. Examples include, but are not limited to, toluene, phenylene, naphthylene, tetrahydronaphthylene, indenylene, indanylene, pentalenylene, fluorenylene and the like, preferably toluene, phenylene or indanylene.

As used herein, the term "aryl" means a monofunctional mono- or dicyclic aromatic system, preferably with 6 to 12 carbon atoms, preferably a monocyclic aromatic system. Examples include, but are not limited to, toluyl, phenyl, naphthyl, tetrahydronaphthyl, indenyl, indanyl, pentalenyl, fluorenyl and the like, preferably toluyl, phenyl or indanyl.

As used herein, the term "heterocyclic group" means a "heterocyclic aliphatic group" or a "heterocyclic aromatic group"

As used herein, the term "heterocyclic aliphatic group" means a difunctional saturated ring system which, in addition to carbon atoms, comprises one, two or three atoms selected from nitrogen, oxygen and/or sulfur. Preferred heterocyclic aliphatic groups are those containing 3 to 5 carbon atoms and one nitrogen, oxygen or sulfur atom.

As used herein, the term "heterocyclic aromatic group" means a monocyclic aromatic 5- or 6-membered ring, which comprises one, two or three atoms selected from nitrogen, oxygen and/or sulfur, or a bicyclic aromatic group comprising two 5- or 6-membered rings, in which one or both rings can contain one, two or three atoms selected from nitrogen, oxygen or sulfur. Examples include, but are not limited to pyridyl, pyrazinyl, pyrimidinyl, pyridazinyl, oxazolyl, oxydiazolyl, isoxazolyl, thiadiazolyl, tetrazolyl, pyrazolyl, imidazolyl, thiazolyl, thienyl, quinolinyl, isoquinolinyl, cinnolinyl, pyrazolo[1,5-a]pyridyl, imidazo[1,2-a]pyridyl, quinoxalinyl, benzothiazolyl, benzotriazolyl, indolyl, indazolyl.

As used herein the term "bridged multicyclic group" means a group consisting of at least two groups selected from the following: monocarbocyclic aromatic groups, dicarbocyclic aromatic groups, cycloalkylene groups; wherein these groups are linked to each other by direct carbon-carbon bonds or by divalent groups.

Preferred divalent groups are oxy-group, thio-group, alkylene-group with 1 to 3 carbon atoms, sulfone-group, methanone-group, and the following groups:

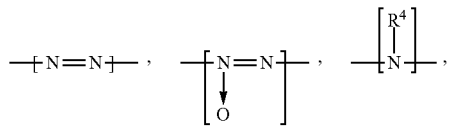

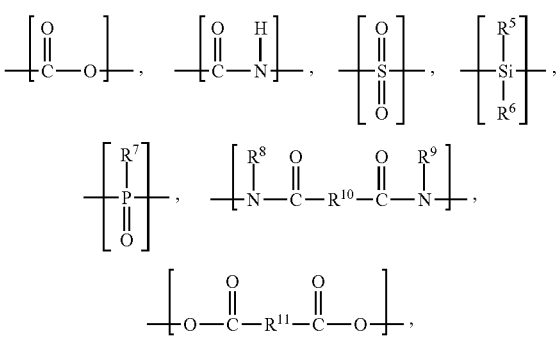

wherein $R^4$, $R^5$, $R^6$, $R^7$, $R^8$, $R^9$ are independently an alkyl group with 1 to 6 carbon atoms; and $R^{10}$ and $R^{11}$ are independently alkylene groups with 1 to 6 carbon atoms.

In one embodiment the term "bridged multicyclic group" means a group consisting of two monocarbocyclic aliphatic groups, which are linked to each other by a direct carbon-carbon bond or by a divalent group such as oxy-group, thio-group, alkylene-group with 1 to 3 carbon atoms, sulfone-group, methanone-group, or one of the following groups:

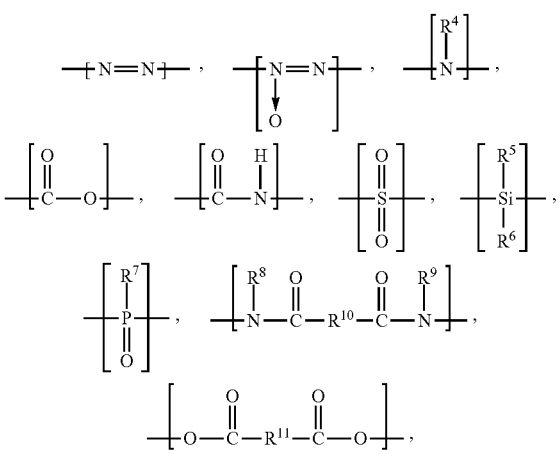

wherein $R^4$, $R^5$, $R^6$, $R^7$, $R^8$, $R^9$ are independently alkyl groups with 1 to 6 carbon atoms; and $R^{19}$ and $R^{11}$ are independently alkylene groups with 1 to 6 carbon atoms.

In one embodiment the term "bridged multicyclic group" means a group consisting of two cyclohexylene groups, which are linked to each other by a direct carbon-carbon bond or by a divalent group such as oxy-group, thio-group, alkylene-group with 1 to 3 carbon atoms, sulfone-group, methanone-group.

In one embodiment the term "bridged multicyclic group" means a group consisting of two monocarbocyclic aromatic groups, which are linked to each other by a direct carbon-carbon bond or by a divalent group such as oxy-group, thio-group, alkylene-group with 1 to 3 carbon atoms, sulfone-group, methanone-group, or one of the following groups:

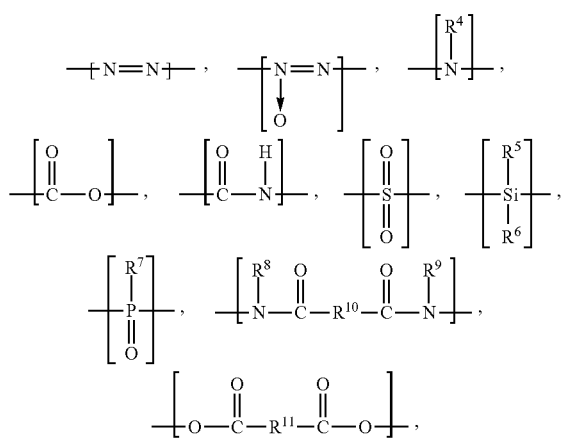

wherein $R^4$, $R^5$, $R^6$, $R^7$, $R^8$, $R^9$ are independently alkyl groups with 1 to 6 carbon atoms; and
$R^{10}$ and $R^{11}$ are independently alkylene groups with 1 to 6 carbon atoms.

In one embodiment the term "bridged multicyclic group" means a group consisting of two phenylene groups, which are linked to each other by a direct carbon-carbon bond or by a divalent group such as oxy-group, thio-group, alkylene-group with 1 to 3 carbon atoms, sulfone-group, methanone-group.

As used herein, the addition of the terms "unsubstituted" or "substituted" means that the respective groups are unsubstituted or carry from 1 to 4 substituents selected from the following: alkyl, alkoxy, halogen. Preferred substituents are methyl or ethyl.

As used herein, the terms "x-functional group", "y-functional group", "y'-functional group" and "y"-functional group" respectively, denote a group, which is bonded to the remainder of the compound via x, y, y', or y" bond(s), respectively. Preferably, the "x-functional group", "y-functional group", "y'-functional group" and "y"-functional group" is a difunctional group, i.e. x, y, y' and y" are preferably 2.

As used herein, the term "difunctional group" means a group, which is bonded to the remainder of the compounds via two bonds. Difunctional groups include but are not limited to, difunctional aliphatic groups and difunctional aromatic groups. Difunctional aliphatic groups include but are not limited to the following groups:

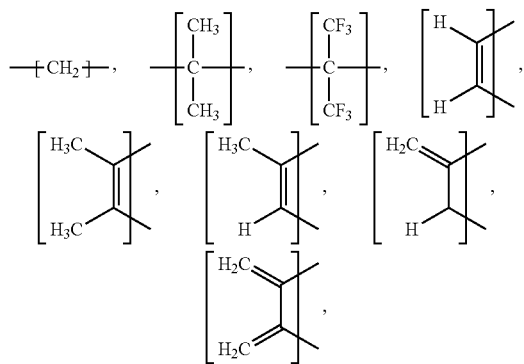

Difunctional aromatic groups include but are not limited to the following groups:

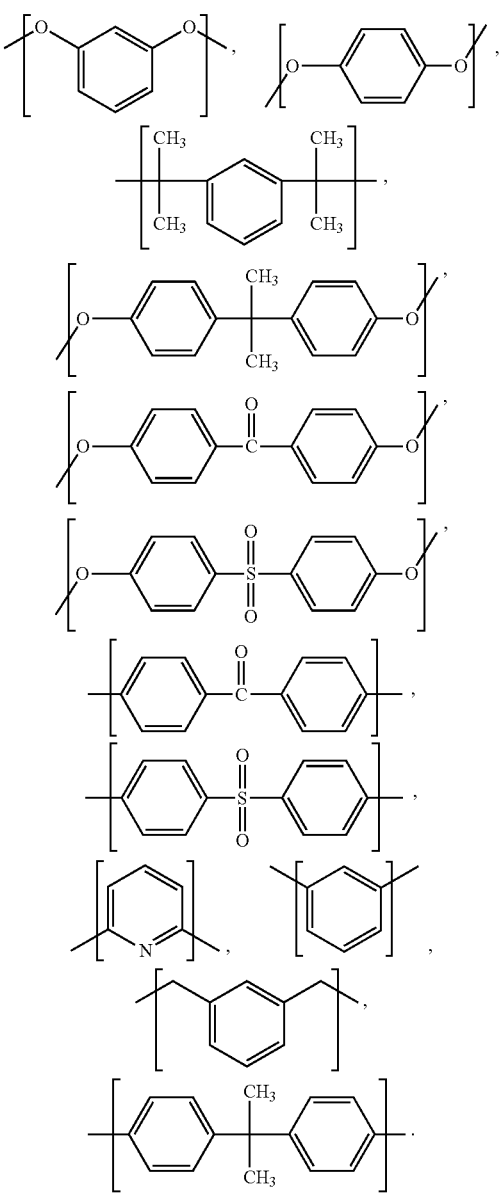

Further difunctional groups include, but are not limited to the following groups:

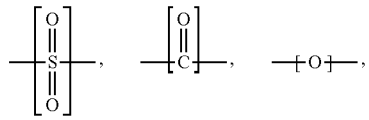

As used herein, the term "Glass transition temperature" or "Tg" means the temperature of reversible transition of an amorphous solid, e.g. polymer, between high elastic state and vitreous (glassy) state, when the polymer becomes brittle on cooling, or soft on heating. More specifically, it defines a pseudo second order phase transition, in which a supercooled melt yields, on cooling, a glassy structure and properties similar to those of crystalline materials, e.g. of an isotropic solid material.

EXAMPLES

The following examples are intended to illustrate but not to limit the invention.

Examples

A. Synthesis of Alkenylphenoxy-Substituted 1,1-diphenylethylenes of Formula (I)

Example 1

Synthesis of 1-phenyl-1-[4-[2-(1-propen-1-yl)phenoxy]phenyl]ethylene (Route 1)

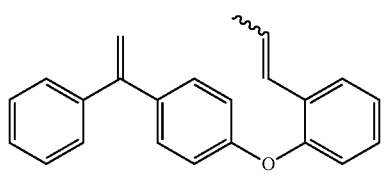

159.5 g (0.45 mol) of methyltriphenylphosphonium bromide and 370 ml of dry tetrahydrofuran were charged into a 3-necked glass reactor, equipped with a stirrer and thermometer, and cooled down to 0° C. 50.1 g (0.45 mol) of potassium tert-butoxide were added to the stirred mixture within 10 min. 117 g (0.37 mol) of 4-[2-(1-propen-1-yl)phenoxy]benzophenone, dissolved in 160 ml of dry tetrahydrofuran, were added within 60 min at max. 8° C. and the mixture was stirred for additional 60 min at ambient temperature. The mixture was then heated for additional 60 min at 45° C. 120 ml of water were added to the mixture and then tetrahydrofuran was stripped off at a temperature of 50° C. under reduced pressure. 300 ml of petroleum ether (80/110) were then added and stirred for 10 min at 50° C. 200 ml of water were then added and the mixture was stirred for 20 min. The precipitate (triphenylphosphine oxide, TPO) was filtered off, phases were separated, and the organic phase was washed with water until pH ca. 7. Additional TPO, which may have precipitated, was filtered off and the solution was dried over anhydrous Na₂SO₄ and filtered through Celite. The solvent was stripped off using a rotary evaporator, and the residue finally was degassed under reduced pressure of 15 Torr at 120° C. for 20 min to yield 111.3 g (82.9%) of a viscous, pale yellow oil. Purity (HPLC, 254 nm): 96.49 area-%. The product also contained 0.20% of TPO and 1.14% of the starting ketone.

Example 1a

Synthesis of 1-phenyl-1-[4-[2-(1-propen-1-yl)phenoxy]phenyl]ethylene (Route 1)

Step 1: Synthesis of phenylmethyl-[2-(1-propen-1-yl)phenoxyphenyl]carbinol

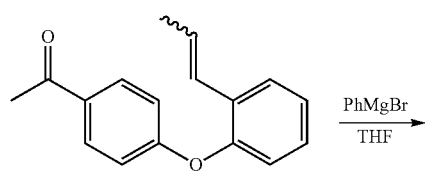

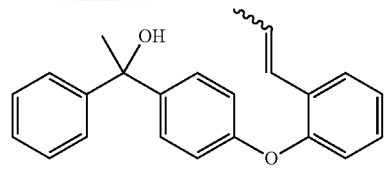

To a solution of 18.65 g (0.067 mol) of tetrabutylammonium bromide in 134.2 g (1.0 mol) of diethyleneglycol dimethyl ether, cooled down to 0° C., was added a solution of 159.5 g (1.0 mol) of phenylmagnesium bromide (as 2.9 M solution in 2-methyltetrahydrofuran) at 0 to 10° C. The suspension was cooled down to 0-2° C. and a solution of 169 g (0.67 mol) 4-[2-(1-propen-1-yl)phenoxy]acetophenone dissolved in 30 ml of dry tetrahydrofuran was slowly added. The mixture was then stirred for 2 hours at 0-5° C. and for additional 4 hours at ambient temperature (20-23° C.). Then the reaction mixture was added to 600 ml of water while stirring within 45 min at max. 15° C. To the resulting suspension were added 200 ml of a saturated aqueous solution of ammonium chloride and 400 ml of toluene. Subsequently, 120 ml of hydrochloric acid (ca. 18 wt.-%) were added to adjust pH to 6. The lower aqueous phase was separated and the organic phase was washed 3 times with 100 ml of water. The toluene phase was dried over anhydrous CaCl₂, filtered, and the solvent was stripped off under reduced pressure using a rotary evaporator. Finally, the product was degassed under reduced pressure of 15 Torr at 120° C. for 20 min to yield 205.3 g (92.8%) of carbinol as a brown highly viscous oil.

Step 2: Dehydration of phenylmethyl-[2-(1-propen-1-yl)phenoxyphenyl]carbinol

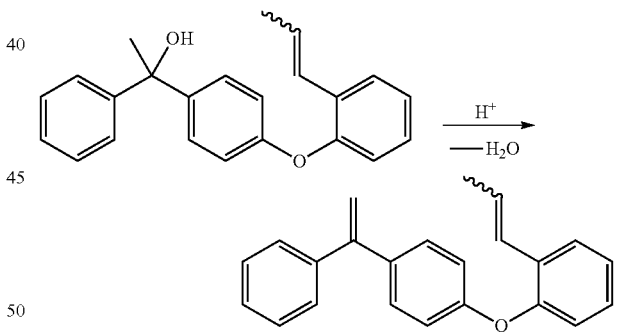

To 200 g of phenylmethyl-[2-(1-propen-1-yl)phenoxyphenyl]carbinol dissolved in 400 ml of toluene were added 2.5 g of p-toluene sulfonic acid and the mixture was heated to between 90° C. and 113° C. while water was azeotropically distilled off within 1.5 hours. 200 ml of sodium hydroxide (10 wt.-%) were added, and the mixture was heated to 50° C. and stirred for 1 hour. The aqueous phase was separated at room temperature. 100 ml of water and 18 ml of hydrochloric acid (18 wt.-%) were added, stirred for 30 min, and the aqueous phase was then separated. The organic phase was washed 3 times with 100 ml of water. The organic phase was dried over anhydrous CaCl₂ and filtered. The solvent was distilled off under reduced pressure using a rotary evaporator. Finally, the product was degassed under reduced pressure of 15 Torr at 120° C. for 20 min to yield 178 g (95%) of light brown viscous oil. Purity (HPLC, 254 nm): 87.14 area-%. The product also contained 7.3% of the intermediate carbinol (product of step 1).

Example 2

Synthesis of 1-phenyl-1-[4-(2-methoxy-4-(1-propen-1-yl)phenoxy)phenyl]ethylene

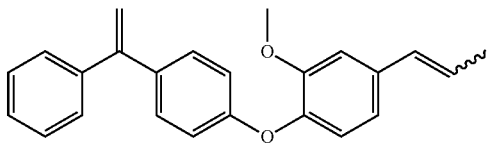

168 g (0.47 mol) of methyltriphenylphosphonium bromide and 390 ml of dry tetrahydrofuran were charged into a 3-necked glass reactor, equipped with a stirrer and thermometer, and cooled down to 0° C. Then 53 g (0.47 mol) of potassium tert-butoxide were added to the stirred mixture within 10 min. 135 g (0.39 mol) of 4-(2-methoxy-4-(1-propen-1-yl)phenoxy)benzophenone dissolved in 170 ml of dry tetrahydrofuran were added within 75 min at a temperature between −5° C. and 1° C. The mixture was then stirred for additional 120 min at ambient temperature. 165 ml of water was added, the mixture was stirred for 10 min and the aqueous phase was separated. Tetrahydrofuran was stripped off at a temperature of max. 60° C. under reduced pressure of max. 100 mbar. 300 ml of petroleum ether 80/110 were then added to the suspension and stirred for 10 min at 30-40° C. The precipitate (TPO) was filtered off, phases were separated, and the organic phase was washed with water until pH ca. 7. Additional TPO, which may have precipitated, was filtered off and the solution was dried over anhydrous $Na_2SO_4$ and filtered through Celite. The solvent was stripped off using a rotary evaporator, and the residue finally was degassed under reduced pressure of 15 Torr at 120° C. for 20 min to yield 119.8 g (89.7%) of a viscous, pale yellow oil. Purity (HPLC, 254 nm): 93.25 area-%. The product also contained 0.39% of TPO and 0.86% of the starting ketone.

Example 3

Synthesis of 1-phenyl-1-[4-[2-(1-propen-1-yl)phenoxy]phenyl]-2-methylethylene

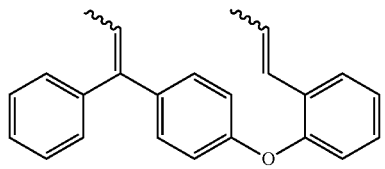

207 g (0.56 mol) of ethyltriphenylphosphonium bromide and 370 ml of dry tetrahydrofuran were charged into a 3-necked glass reactor, equipped with a stirrer and thermometer, and cooled down to 0° C. 62.5 g (0.56 mol) of potassium tert-butoxide were added to the stirred mixture within 10 mins. 117 g (0.37 mol) of 4-[2-(1-propen-1-yl)phenoxy]benzophenone dissolved in 160 ml of dry tetrahydrofuran were added within 60 mins at max. 8° C. The mixture was then stirred for additional 120 min at ambient temperature. 160 ml of water were added to the mixture and then tetrahydrofuran was stripped off at a temperature of 50° C. under reduced pressure. 300 ml of petroleum ether (80/110) were then added, and the mixture was stirred for 10 min at 50° C. 200 ml of water were then added and the mixture was stirred for 20 mins. The precipitate (TPO) was filtered off, phases were separated, and the organic phase was washed with water until pH 7. Additional TPO, which may have precipitated, was filtered off, and the solution was dried over anhydrous $Na_2SO_4$ and filtered through Celite. The solvent was stripped off using a rotary evaporator, and the residue finally was degassed under reduced pressure of 15 Torr at 130° C. for 20 min to yield 132 g (96%) of a viscous, pale yellow oil. Purity (HPLC, 254 nm): 95.45 area-%. The product also contained 0.41% of TPO and 0.96% of the starting ketone.

Example 4

Synthesis of 1-phenyl-1-[4-[2-methoxy-4-(1-propen-1-yl)phenoxy]phenyl]-2-propylethylene

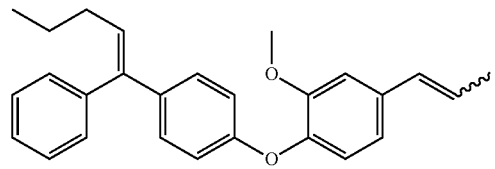

168 g (0.47 moles) of butyltriphenylphosphonium bromide and 390 ml of dry tetrahydrofuran were charged into a 3-necked glass reactor, equipped with a stirrer and thermometer, and cooled down to 0° C. 53 g (0.47 moles) of potassium tert-butoxide were added to the stirred mixture within 10 min. 134.9 g (0.39 moles) of 4-[2-methoxy-4-(1-propen-1-yl)phenoxy]benzophenone dissolved in 180 ml of dry tetrahydrofuran were added within 75 min at a temperature between 0° C. and 5° C. The mixture was then stirred for additional 120 min at 20-45° C. 150 ml of water was added to the mixture and stirred for 10 min. The aqueous phase was separated and tetrahydrofuran was stripped off at a temperature of max. 50° C. under reduced pressure. 300 ml of petroleum ether (80/110) were then added to the residue, and the mixture was stirred for 10 min at 30-40° C. 150 ml of water were then added and the mixture was stirred for 10 min at ambient temperature. The precipitate (TPO) was filtered off, phases were separated, and the organic phase was washed with water until pH 7. Additional TPO, which may have precipitated, was filtered off and the solution was dried over anhydrous $Na_2SO_4$ and filtered through Celite. The solvent was stripped off using a rotary evaporator, and the residue finally was degassed under reduced pressure of 15 Torr at 120° C. for 20 min to yield 164.5 g (102%) of a viscous, pale yellow oil. Purity (HPLC, 254 nm): 91.48 area-%. The product also contained 0.52% of TPO and 2.01% of the starting ketone.

Example 5

Synthesis of 1,1-bis-[4-[2-(1-propen-1-yl)phenoxy]phenyl]-2-methylethylene

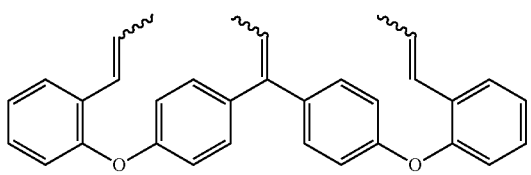

133.7 g (0.36 moles) of ethyltriphenylphosphonium bromide and 300 ml of dry tetrahydrofuran were charged into a 3-necked glass reactor, equipped with a stirrer and thermometer, and cooled down to 2° C. 40.4 g (0.36 moles) of potassium tert-butoxide were added to the stirred mixture within 10 min. 134 g (0.3 mol) of 4,4'-bis-[2-(1-propen-1-yl)phenoxy]benzophenone dissolved in 180 ml of dry tetrahydrofuran were added within 120 min at a temperature between 0° C. and 8° C. The mixture was then stirred for additional 180 mins at 20-45° C. 100 ml of water were added and the mixture was stirred for 10 min. Tetrahydrofuran was stripped off at a temperature of max. 50° C. under reduced pressure. 300 ml of petroleum ether (80/110) were added to the residue, and the mixture was then stirred for 10 min at 30-40° C. Subsequently, 200 ml of water was added and the mixture was stirred for 30 min at ambient temperature. The precipitate (TPO) was filtered off, phases were separated, and the organic phase was washed with water until pH 7. Additional TPO, which may have precipitated, was filtered off and the solution was dried over anhydrous $Na_2SO_4$ and filtered through Celite. The solvent was stripped off using a rotary evaporator, and the residue finally was degassed under reduced pressure of 15 Torr at 140° C. for 20 min to yield 131 g (92.9%) of a viscous, pale yellow oil. Purity (HPLC, 254 nm): 91.45 area-%. The product also contained 0.40% of TPO and 1.75% of the starting ketone.

Example 6

Synthesis of 1,1-bis-[4-[2-(1-propen-1-yl)phenoxy]phenyl]-ethylene

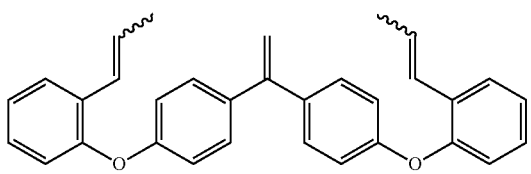

128.6 g (0.36 moles) of methyltriphenylphosphonium bromide and 300 ml of dry tetrahydrofuran were charged into a 3-necked glass reactor, equipped with a stirrer and thermometer, and cooled down to 2° C. 40.4 g (0.36 moles) of potassium tert-butoxide were added to the stirred mixture within 10 min. 134 g (0.3 mol) of 4,4'-bis-[2-(1-propen-1-yl)phenoxy]benzophenone dissolved in 180 ml of dry tetrahydrofuran were added within 120 min at a temperature between 0° C. and 8° C. After that, the mixture was stirred for additional 180 min at 20-45° C. Then 120 ml of water were added and the mixture was stirred for 10 mins. Tetrahydrofuran was stripped off at a temperature of max. 50° C. under reduced pressure. 300 ml of petroleum ether (80/110) were then added to the residue, and the mixture was stirred for 10 min at 30-40° C. Subsequently, 200 ml of water were added and the mixture was stirred for 30 min at ambient temperature. The precipitate (TPO) was filtered off, phases were separated, and the organic phase was washed with water until pH 7. Additional TPO, which may have precipitated, was filtered off and the solution was dried over anhydrous $Na_2SO_4$ and filtered through Celite. The solvent was stripped off using a rotary evaporator, and the residue finally was degassed under reduced pressure of 15 Torr at 110° C. for 20 min to yield 118 g (88.5%) of a viscous, pale yellow oil, which solidified at room temperature. Purity (HPLC, 254 nm): 93.40 area-%. The product also contained 0.16% of TPO and 0.64% of the starting ketone.

B. Preparation of Curable Mixtures of this Invention Based on Polymaleimide (IV) and alkenylphenoxy-substituted 1,1-diphenylethylenes of Formula (I)

The curable mixtures of the invention were obtained according to the following general processes:
(a) Melt Process At least one polymaleimide of formula (IV), at least one alkenylphenoxy-substituted 1,1-diphenylethylene (I) and, if required, at least one additional co-monomer component were melt-blended in a temperature range of 120-140° C. until a clear melt was obtained. Subsequently, the melt thus obtained was further heated in the same temperature range for a time sufficient to obtain a stable melt. Finally, the melt was degassed under reduced pressure of 20 hPa [15 mm Hg] for 2-10 minutes to obtain a curable mixture.
(b) Solvent-Assisted Process At least one polymaleimide of formula (IV) and at least one alkenylphenoxy-substituted 1,1-diphenylethylene (I) and, if required, at least one additional co-monomer component and an organic solvent, preferably toluene, in a weight ratio solid-to-solvent of 1:1 were heated up to 90-100° C. until a clear solution was obtained. Subsequently, the solvent was stripped off under reduced pressure, and the temperature was simultaneously increased to 120° C. Finally, the mixture was degassed for 30 minutes under reduced pressure of 20 hPa [15 mm Hg] to obtain a curable mixture. The resin/solvent ratio may vary, depending on the solubility of components. Other solvents or diluents, as mentioned in the patent, may also be used.
(c) Reactivity Measurements
(c.1) Differential Scanning Calorimetry (DSC)

Differential scanning calorimetric (DSC) traces, obtained at a defined heating rate (10° C./min) in the temperature range from 20 to 380° C., were used to characterize the cure kinetics of curable compositions of the present invention. The cure exothermic maximum, $T_{MAX}$, represents the temperature of maximum heat release at the specified heating rate. The higher is $T_{MAX}$ the slower is the cure of a resin. The $T_{MAX}$ data of curable compositions of bismaleimides of formula (IV) and alkenylphenoxy-substituted 1,1-diphenylethylenes of formula (I), prepared in examples 7 through 16, are compiled in Table 1.
(c.2) Hot-Plate Gel Time Being a standard measure of resin reactivity, the gel time was measured by placing 1 g of the resin on an electrically heated metal block with a polished surface, which is capable of being maintained at temperatures between 130° C. and 230° C., and continuous stirring and probing the molten sample with a wooden rod, as described in the ISO 8987 and ASTM D4217 norms. The gelation results of curable compositions of bismaleimides of formula (IV) and alkenylphenoxy-substituted 1,1-diphenylethylenes of formula (I), prepared in examples 7 through 16, are compiled in Table 1.

C. Curable polymaleimide/alkenylphenoxy-1,1-diphenyethylene Mixtures

Examples 7 Through 15

TABLE 1

Reactivity data of curable compositions of BMI (IV) and alkenylphenoxy-1,1-diphenylethylenes (I). Molar ratio of all BMI (IV)/co-monomer (I) mixtures was 1.0:0.7 mol/mol, respectively. DSC heating rate 10° C./min.

| Example No. | Co-monomer (I) from Example No. | Bismaleimide BMI (IV) | DSC $T_{MAX}$ (° C.) | Gel time at T (sec) 150° C. | 170° C. |
|---|---|---|---|---|---|
| 7 | 1 | MDAB | 151 | 155 | 81 |
| 8 | 2 | MDAB | 166 | 151 | 64 |
| 9 | 3 | MDAB | 196 | 595 | 192 |
| 10 | 4 | MDAB | 193 | 702 | 217 |
| 11 | 4 | C353A | 207 | 1747 | 475 |
| 12 | 5 | MDAB | 189 | 349 | 125 |
| 13 | 5 | MXBI | 188 | 360 | 150 |
| 14 | 5 | C353A | 195 | 840 | 210 |
| 15 | 6 | MDAB | 151 | 139 | 62 |

MDAB = 4,4'-bismaleimidodiphenylmethane;
MXBI = m-xylylene bismaleimid;
C353A = eutectic mixture of 4,4'-bismaleimidodiphenylmethane, 2,4-bismaleimidotoluene, and 1,6-bismaleimido-2,2,4(4,4,2)-trimethylhexane stabilized with hydroquinone, commercial bismaleimide mixture available from Evonik Industries.

Comparative Examples 16 and 17

TABLE 2

Comparative reactivity data of BMI(IV)/commercial co-monomer mixtures. Molar ratio of all BMI (VI)/co-monomer comparative mixtures was 1.0:0.7 mol/mol, respectively. DSC heating rate 10° C./min.

| Example No. | Comparative co-monomer | Bismaleimide BMI (II) | DSC $T_{MAX}$ (° C.) | Gel time at T (sec) 150° C. | 170° C. |
|---|---|---|---|---|---|
| 16 | TM123 | MDAB | 229 | 3914 | 844 |
| 17 | TM124 | MDAB | 258 | 5410 | 1705 |

TM124 = o,o'-diallylbisphenol-A (commercial product available from Evonik Industries);
TM123 = 4,4'-bis(o-propenylphenoxy)benzophenone (commercial product available from Evonik Industries);
MDAB = 4,4'-bismaleimidodiphenylmethane.

Comparison of gel time data of examples 7 to 15 (Table 1) with the corresponding gel time data of examples 16 and 21 (non-alkenylphenoxy-1,1-diphenylethylenes (I) based mixtures, Table 2) clearly demonstrates significantly faster curing obtained for the mixtures comprising the alkenylphenoxy-1,1-diphenylethylenes (I) type co-monomers of this invention. The results obtained by differential scanning calorimetry (DSC), are in accord with the results obtained from gel time measurements. DSC maxima of the corresponding formulations, $T_{max}$, were found at lower temperatures, for the faster curing mixtures comprising the alkenylphenoxy-1,1-diphenylethylenes (I) type co-monomers of this invention.

While the invention has been described in detail, modifications in the spirit and scope of the invention will be readily apparent to those of skill in the art. Those of ordinary skill in the art will appreciate that the foregoing description is by way of example only, and is not intended to limit the invention.

The invention claimed is:

1. An alkenylphenoxy-1,1-diphenylethylene of formula (I):

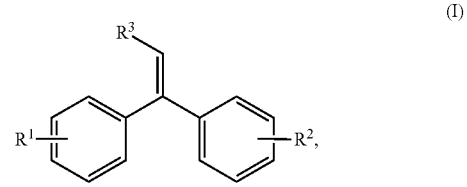

wherein:

$R^1$ is hydrogen or an alkenylphenoxy group, $R^2$ is an alkenylphenoxy group, and $R^3$ is hydrogen or an alkyl group with 1 to 4 carbon atoms.

2. The alkenylphenoxy-1,1-diphenylethylene of claim 1, wherein alkenylphenoxy groups $R^1$ and $R^2$ are independently selected from the group consisting of the following structures:

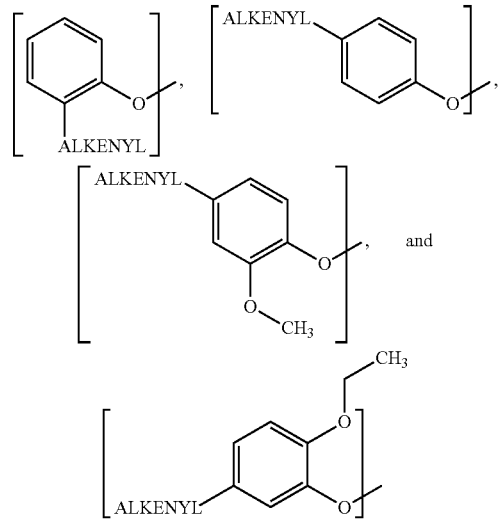

in which the ALKENYL residue is a 1-alkenyl group with 2 to 6 carbon atoms or a 2-alkenyl group with 3 to 6 carbon atoms.

3. A curable composition, comprising:
(a) at least one alkenylphenoxy-diphenylethylene according to claim 1; and (b) at least one polyimide of formula (II):

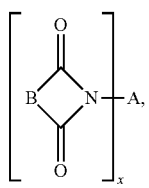
(II)

wherein:
B is a difunctional group containing a carbon-carbon double bond, and
A is an x-functional group, and
x is an integer ≥2.

4. The curable composition according to claim 3, wherein B in the polyimide according to formula (II) is selected from the group consisting of the following difunctional groups:

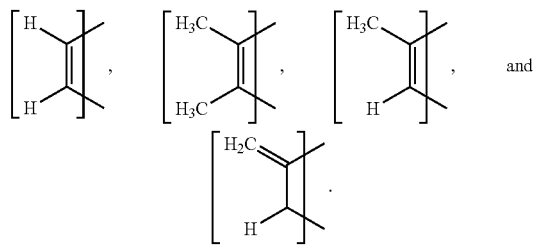

5. The curable composition according to claim 3, wherein the x-functional group A in the polyimide of formula (II), is selected from the group consisting of:
a) alkylene group with 2 to 12 carbon atoms;
b) cycloalkylene group with 5 to 6 carbon atoms;
c) heterocyclic group with 4 to 5 carbon atoms and at least one nitrogen, oxygen, or sulphur atom in the ring;
d) mono- or dicarbocyclic group;
e) bridged multicyclic group consisting of at least two groups selected from the following: monocarbocyclic aromatic groups, dicarbocyclic aromatic groups, cycloalkylene groups; wherein these groups are linked to each other by direct carbon-carbon bonds or by divalent groups; and
f) a group defined by formula (III):

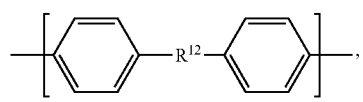
(III)

wherein $R^{12}$ is one of the following groups:

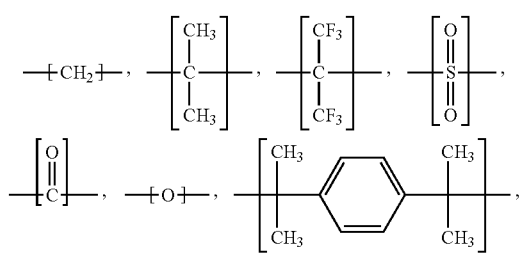

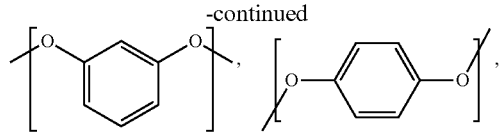

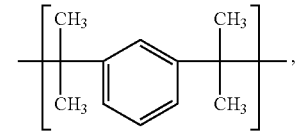

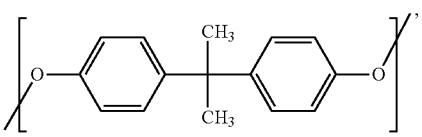

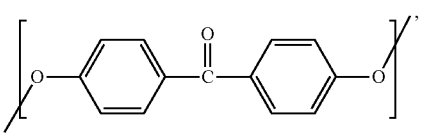

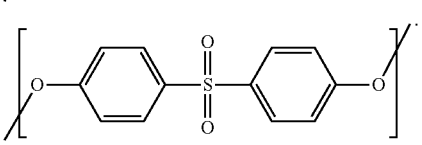

6. The curable composition according to claim 3, wherein the polyimide of formula (II) is selected from the group consisting of 4,4'-bismaleimidodiphenylmethane, bis(3-methyl-5-ethyl-4-maleimidophenyl)methane, bis(3,5-dimethyl-4-maleimidophenyl)methane, 4,4'-bismaleimidodiphenylether, 4,4'-bismaleimidodiphenylsulfone, 3,3'-bismaleimidodiphenylsulfone, bismaleimidodiphenylindane, 2,4-bismaleimidotoluene, 2,6-bismaleimidotoluene, 1,3-bismaleimidobenzene, 1,2-bismaleimidobenzene, 1,4-bismaleimidobenzene, 1,2-bismaleimidoethane, 1,6-bismaleimidohexane, 1,6-bismaleimido-(2,2,4-trimethyl) hexane, 1,6-bis maleimido-(2,4,4-trimethyl)hexane, 1,4-bis(maleimidomethyl)cyclohexane, 1,3-bis(maleimidomethyl)cyclohexane, 1,4-bismaleimidodicyclohexylmethane, 1,3-bis(maleimidomethyl)benzene, and 1,4-bis(maleimidomethyl)benzene.

7. A process for manufacturing the curable composition of claim 3, the process comprising blending components (a) and (b) with a powder-, melt-, or solvent assisted blending process resulting in a solid, low-melting, or tacky curable composition.

8. A curable prepolymer obtained from the curable composition according to claim 3, by a process comprising heating the curable composition to a temperature ranging from 50° C. to 250° C. for a time sufficient to obtain a prepolymer, which is still formable upon the application of heat, pressure, or both.

9. A crosslinked polymer obtained from the curable composition according to claim 3 by a process comprising heating the curable composition to a temperature ranging from 70° C. to 280° C. for a time sufficient to obtain a polymer.

10. A process for manufacturing a composite material, the process comprising combining the curable composition according to claim 3, with a fibrous or particulate reinforcement, and curing the resultant product.

11. A composite material obtained by the process according to claim 10.

12. The curable composition according to claim 5, wherein the x-functional group A in the polyimide of formula (II) is
  e) bridged multicyclic group consisting of at least two groups selected from the following: monocarbocyclic aromatic groups, dicarbocyclic aromatic groups, cycloalkylene groups;
  these groups are linked to each other by direct carbon-carbon bonds or by divalent groups, and
  the divalent groups are selected from the following: oxy-group, thio-group, alkylene-group with 1 to 3 carbon atoms, sulfone-group, methanone-group, or one of the following groups:

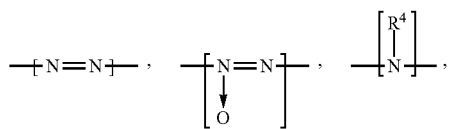

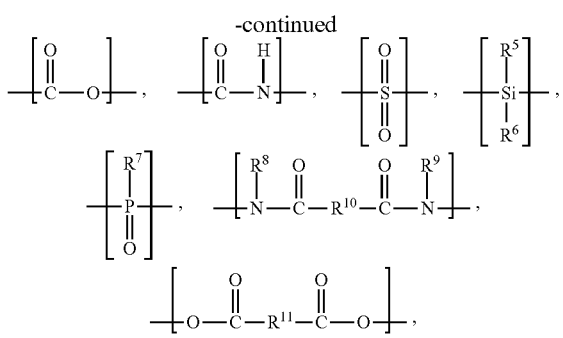

wherein
$R^4$, $R^5$, $R^6$, $R^7$, $R^8$, $R^9$ are independently alkyl groups with 1 to 6 carbon atoms; and
$R^{10}$ and $R^{11}$ are independently alkylene groups with 1 to 6 carbon atoms.

* * * * *